(12) United States Patent
Cowan et al.

(10) Patent No.: US 7,279,684 B2
(45) Date of Patent: Oct. 9, 2007

(54) METHOD USING NIR SPECTROSCOPY TO MONITOR COMPONENTS OF ENGINEERED WOOD PRODUCTS

(75) Inventors: Jennifer J. Cowan, Atlanta, GA (US); Albert G. Landers, Dacula, GA (US)

(73) Assignee: Huber Engineered Woods LLC, Charlotte, NC (US)

( * ) Notice: Subject to any disclaimer, the term of this patent is extended or adjusted under 35 U.S.C. 154(b) by 59 days.

(21) Appl. No.: 11/301,030

(22) Filed: Dec. 13, 2005

(65) Prior Publication Data

US 2007/0131862 A1 Jun. 14, 2007

(51) Int. Cl.
G01N 21/35 (2006.01)
(52) U.S. Cl. .................................. 250/339.09
(58) Field of Classification Search ............... 264/410; 250/339.09
See application file for complete search history.

(56) References Cited

U.S. PATENT DOCUMENTS

| | | |
|---|---|---|
| 4,345,150 A | 8/1982 | Tamura et al. |
| 4,692,620 A | 9/1987 | Rosenthal |
| 5,044,755 A | 9/1991 | Landa et al. |
| 5,155,184 A | 10/1992 | Laurent et al. |
| 5,291,422 A | 3/1994 | Esztergar |
| 5,339,255 A | 8/1994 | Suzuki et al. |
| 5,436,456 A | 7/1995 | Tucker et al. |
| 5,532,487 A | 7/1996 | Brearley et al. |
| 5,573,952 A | 11/1996 | Moessner |
| 5,837,786 A | 11/1998 | Miyoshi et al. |
| 5,965,888 A | 10/1999 | Engström et al. |
| 6,281,500 B1 | 8/2001 | Gaon |
| 6,300,633 B1 | 10/2001 | Hunt et al. |
| 6,414,312 B1 | 7/2002 | Nordin et al. |
| 6,630,672 B1 | 10/2003 | Brotherton et al. |
| 6,639,044 B2 | 10/2003 | Dessipri et al. |
| 6,841,779 B1 | 1/2005 | Roehner et al. |
| 6,846,446 B2 | 1/2005 | Mbachu et al. |
| 6,846,447 B2 | 1/2005 | Mbachu et al. |
| 2002/0053640 A1 | 5/2002 | Kester et al. |
| 2004/0094851 A1 | 5/2004 | Mbachu et al. |
| 2005/0027044 A1 | 2/2005 | Moriarty et al. |
| 2005/0067569 A1 | 3/2005 | Shelley et al. |
| 2005/0140037 A1 | 6/2005 | Mbachu et al. |
| 2005/0241743 A1* | 11/2005 | Mbachu et al. ............... 156/64 |

OTHER PUBLICATIONS

Bruce M. Broline, Reginald A. Mbachu, and Tyler G. Congleton, "Visible-Near Infrared Monitoring of Resin Loading Prior to the Assembly of Engineering Wood Products," Presented at the Wood Adhesives Conference, San Diego, California, Nov. 2-4, 2005, 24 pages.*
Ellen V. Nagy, Jeff Balogh, and Robert Meacham, "Application of Near Infrared Spectroscopy to Resin/Wax Adhesive Systems," Poster 3 presented at the Wood Adhesives Conference, San Diego, California, Nov. 2-4, 2005, abstract.*
The NIR Desk Reference, Mar. 1998, pp. 1-47, Publication No. 1-K98002A, LT Industries Inc., Gaithersburg, Maryland USA.

* cited by examiner

*Primary Examiner*—Constantine Hannaher
(74) *Attorney, Agent, or Firm*—Carlos Nieves; Raymond Hoch; Patricia Ades (57) ABSTRACT

Method of use of near infrared (NIR) spectroscopy for quantitative analysis of resin-wood composites, and methods of making engineered wood products using calibrated near infrared (NIR) spectroscopic instrumentation for quantitative analysis of resin-wood composites.

22 Claims, 3 Drawing Sheets

METHOD USING NIR SPECTROSCOPY TO MONITOR COMPONENTS OF ENGINEERED WOOD PRODUCTS

FIELD OF THE INVENTION

This invention relates to use of near infrared (NIR) spectroscopy for quantitative analysis of resin-wood composites, and methods of making engineered wood products using calibrated near infrared (NIR) spectroscopic instrumentation for quantitative analysis of resin-wood composites.

BACKGROUND OF THE INVENTION

Resin-wood composites, such as oriented strand board ("OSB"), wafer board, chipboard, fiberboard, etc., are widely used as construction materials, such as for flooring, sheathing, walls, roofing, concrete forming, and so forth. The wood component typically is virgin or reclaimed ligno-cellulosic material, which may be derived from naturally occurring hard or soft woods, singularly or mixed. Typically, the raw wood starting materials are cut into strands, wafers, chips, particles, or other discrete pieces of desired size and shape. These ligno-cellulosic wood materials can be "green" (e.g., having a moisture content of 5-30% by weight) or dried (e.g., having a moisture content of about 2-18 wt %).

In the commercial fabrication of OSB, for instance, multiple layers of raw wood "flakes" or "strands" are bonded together by a resin binder. The flakes or strands used in OSB production have been made by cutting logs into thin slices with a knife edge parallel to the length of a debarked log. The cut slices are broken into narrow strands generally having lengthwise dimensions which are larger than the widths, where the lengths are typically oriented parallel to the wood grain. The flakes are typically 0.01 to 0.05 inches thick, although thinner and thicker flakes can be used in some applications, and are typically, less than one inch to several inches long and less than one inch to a few inches wide. The raw flakes then may be dried. The raw flakes or other ligno-cellulosic wood materials are coated with a polymeric thermosetting binder resin and a sizing agent such as wax, such that the wax and resin effectively coat the wood materials. Conventionally, the binder, wax and any other additives are applied to the wood materials by various spraying techniques. One such technique is to spray the wax, resin and additives upon the wood strands as the strands are tumbled in a drum blender. Binder resin and various additives applied to the wood materials are referred to herein as a coating, even though the binder and additives may be in the form of small particles, such as atomized particles or solid particles, which may not form a continuous coating upon the wood material. After any drying, the flakes are coated with a thin layer of binder material and sizing agent, and then pressed and resin-cured to provide a desired product shape. This coating operation may be performed in a blender. The coated flakes may then be spread on a conveyor belt to provide a first surface ply or layer having flakes oriented generally in line with the conveyor belt, then one or more plies that will form an interior ply or plies of the finished board is (are) deposited on the first ply such that the one or more plies is (are) oriented generally perpendicular to the conveyor belt. Then, another surface ply having flakes oriented generally in line with the conveyor belt is deposited over the intervening one or more plies having flakes oriented generally perpendicular to the conveyor belt. Plies built-up in this manner have flakes oriented generally perpendicular to a neighboring ply insofar as each surface ply and the adjoining interior ply. The layers of oriented "strands" or "flakes" are finally exposed to heat and pressure to bond the strands and binder together. The resulting product is then cut to size and shipped. Typically, the resin and sizing agent comprise less than 10% by weight of the oriented strand board.

Board product uniformity and quality is sensitive to formulation variations. Often, panel components are not measured directly but inferred from application rates. This situation has led to a gap in information about blending efficiency, which limits the ability to improve the process. There is a need for rapid, noninvasive analysis methods for wood composite products. Direct measurement of the amount of adhesive, wax, moisture, or other binder constituents or additives applied to ligno-cellulosic particles, e.g., OSB flakes, has been a time-consuming procedure. This has been accomplished in the past, for example, by elemental analysis or image analysis. While elemental analysis can give accurate measurements on the elements present in samples, a week or more may be required before results are returned from an outside lab. Delayed acquisition of analysis results may limit their usefulness for near-time adjustment of current process parameters such that considerable production may occur before a formulation variation from target conditions is identified. Elemental analysis is also of limited use for discriminating between and determining the concentrations of components whose elemental makeup contains significant carbon, hydrogen, and/or oxygen, since these are also the elements predominant in wood, and the test results do not differentiate between different sources of these elements. Waxes and polyols are two common OSB components that fall into this category. Other methods of wax analysis are in use, but they involve lengthy organic solvent extraction procedures.

Image analysis also has been used to analyze content of OSB composite wood products. Image analysis involves off-line photographing or scanning individual flakes, or paper onto which resin has been transferred, and using a computer to analyze the digital image. The coverage area of a colored material on a lighter-colored background, such as phenol-formaldehyde resin on a flake, is then calculated. This approach works well for colored components, such as phenol-formaldehyde resin, but not for colorless or light colored components such as isocyanate resins, urea-formaldehyde resins, polyols, or waxes. A dye may be added to the component or sprayed on the treated flake.

Spectroscopic techniques also have been described for monitoring ligno-cellulosic board formulations. All organic materials absorb infrared (including near-infrared) light according to Beer's law. Three categories of infrared spectroscopies are commonly recognized, classified by the energy of the light used, comprising: mid-infrared spectroscopy from 2400-25,000 nm, near-infrared (NIR) spectroscopy from 800-2400 nm, and far-infrared spectroscopy from 20,000-66,000 nm. Far IR is typically used for inorganic materials. Quantitative mid-IR analysis can be problematic due to baseline effects and the absorbance of background gases such as water vapor and carbon dioxide. NIR spectroscopy does not suffer from these difficulties, and it is generally faster and requires less sample preparation than mid-IR. NIR instruments are faster than mid-IR instruments because the energy from the lamp is more intense, the detector is more sensitive, and the Beer's law constant is greater in the NIR region.

NIR spectroscopic analysis of adhesive-treated wood flakes is time-dependent, because the adhesives undergo chemical reactions such as polymerization, even at room temperature. These changes in the chemical makeup of the samples result in changes in their spectra, which can make the spectra unsuitable for component concentration predictions which are related to calibrations based on samples that may have been handled differently after sampling. Conducting rapid spectra acquisition on freshly mixed and collected samples can reduce this variable. However, on-the-spot rapid assay strategies may not be practical for many production operations.

NIR technology has been used in the wood industry, most commonly for moisture measurements. However, it may also be used for resin and wax analysis. U.S. Pat. Nos. 6,846,446 and 6,846,447 describe measuring resin content on engineered wood products by near-infrared (NIR) spectroscopy and a method for calibrating the instruments. The '446 and '447 patents measure resin alone, and remove information about moisture content (and other non-resin components) of the samples before spectral data are analyzed for resin content. Representative industrial NIR spectroscopic instruments, such as one from Process Sensors Corporation (Milford, Mass.), measure only at several different wavelengths, or alternatively at narrow bands of wavelengths, rather than an entire NIR spectrum. While measurements at only a few wavelengths may produce reliable calibrations in limited circumstances, these strategies are relatively inflexible.

There also is a need for noninvasive analysis methods for wood composites that can handle aged samples. Ideally, in order to take spectra of recently prepared resin-loaded samples, an NIR instrument or other spectrophotometer would be located on the same site, on-line or off-line, as the source of the production samples. However, it may not be economical for all operations to purchase an instrument for every production site because of the expense and the need for trained instrument operators. Nor is it feasible to ship a NIR instrument from one location to another because of the risk of damage. Even if production samples and the instrument are located on the same production site, there are often impediments to rapidly collecting spectra from production samples. Particularly in a continuous production mode, multiple tasked personnel may need to be available for the sample collection, sample preparation, and analysis processing to get accomplished regularly and rapidly. Such levels of staffing may not be feasible for all operations during all production runs. Methods for analyzing aged wood composite samples which provide results reflecting the fresh sample formulation are needed. Such methods ideally would make it possible to accurately acquire and collect spectra from wood composite production samples independent of the sample's age, time, and sampling location.

As will become apparent from the descriptions that follow, the invention addresses these needs as well as providing other advantages and benefits.

SUMMARY OF THE INVENTION

The invention relates to a method using near infrared (NIR) spectroscopy for quantitative analysis of resin-wood composites. It also relates to a method of making engineered wood products using calibrated near infrared (NIR) spectroscopic instrumentation for quantitative analysis of resin-wood composites.

Embodiments of the present invention make it possible to simultaneously measure concentration of all the non-wood components in a resin-wood composite sample. In particular, embodiments of the present invention make it feasible to simultaneously quantitatively measure resins of different types, wax, moisture and other additives of resin-wood composite, by NIR spectroscopy methods. As any one of the components of resin-wood composite formulations may measurably affect the quality of the panels produced from them, the full compositional analysis results provided by methods of the present invention are highly useful and enhance efficiency in process control for resin-wood composition production. Embodiments of this invention are applicable to performing noninvasive compositional analysis of either uncured or cured resin-wood composite samples.

In one embodiment, a method is provided for determining the composition of a resin-wood composite material in which a plurality of training samples are provided comprising quantitatively predetermined respective amounts of a plurality of components comprising at least wood, resin, moisture, and wax. The training samples are irradiated with NIR radiation using NIR spectroscopic instrumentation including an associated source of NIR radiation. The irradiation step comprises exposing the training samples to NIR radiation at a succession of different wavelength values spanning a selected spectral range of wavelengths including a range of about 1200 nm to about 2400 nm. The non-absorbed NIR energy reflected by said exposed training samples is measured over the selected spectral range at wavelength measuring intervals not exceeding about 5 nm, providing respective training sample spectral data sets. A calibration is developed with reference to the training sample spectral data sets for the NIR spectroscopic instrumentation for quantitatively correlating spectral results with component concentrations in compositions comprising at least wood, resin, moisture, and wax. The calibration is used to perform quantitative analyses on unknown test samples containing a plurality of components comprising at least wood, resin, moisture, and wax. The test sample is irradiated with NIR radiation using the NIR spectroscopic instrumentation, wherein the irradiating comprises exposing the test sample to unfiltered NIR radiation at a succession of different wavelength values spanning a selected spectral range of wavelengths including a range of about 1200 nm to about 2400 nm. The non-absorbed NIR energy reflected by said test sample is measured over said selected spectral range at wavelength measuring intervals not exceeding about 5 nm, providing a test sample spectral data set. The calibration and the test sample spectral data are used to predict the component concentrations of at least resin, moisture, and wax, in the test sample.

In one embodiment, the amounts of the respective components in the training samples are randomly chosen for each training sample within a respective preselected range for each of said components. The training samples and test sample should be provided at approximately the same temperature for the respective steps of irradiating them with NIR radiation. Also, a plurality of scans, e.g., about 20 to about 40 scans, are taken at each measurement interval for the training samples, and the results are averaged to provide a respective average non-absorbed energy value at each given measurement wavelength which are referenced in generating the calibration. Similarly, a plurality of scans, e.g., about 20 to about 40 scans, are taken at each measurement interval for the test sample, and the results are averaged to provide a respective average non-absorbed energy value at each given measurement wavelength that is referenced in the predicting of the component concentrations of the unknown sample.

In one embodiment, the NIR spectroscopic instrumentation comprises a rapid-scanning grating system operable to use a diffraction grating to separate a polychromatic spectrum into constituent wavelengths, such as all individual wavelengths in the 1200-2400 nm range. In one embodiment, the instrument has a PbS photoconductive detector. When the NIR light strikes it, its resistance changes. The magnitude of the change is proportional to the light intensity. In one embodiment, the instrument is controlled to collect data in approximately 1-nm increments. Lower resolution strategies also may be used. In one embodiment, the development or generation of the calibration comprises applying multivariate data analysis to the training sample spectral data sets. The multivariate data analysis may be selected from among partial least squares regression (PLS), principal component analysis (PCA), principal component regression (PCR), multilinear regression analysis (MLR), and particularly may be partial least squares regression (PLS).

In one embodiment, the training sample composition contains a resin including phenol formaldehyde resin and/or isocyanate resin. The sample contains a wood component, which may comprise a wood material selected from the group consisting of wood strands, wood flakes, wood particles, sawdust, wood wafers, and wood fibers.

In another embodiment, it has been discovered that measurement predictability for aged samples is significantly improved by thermally pre-treating training samples and unknown samples at temperatures above room temperature prior to spectroscopic analysis. In one embodiment, the irradiating of the unknown sample occurs at least about four hours, particularly at least about 24 hours, and more particularly about 24 to about 240 hours, after admixture of the components thereof. In one embodiment, the heating of the training samples and the heating of the unknown sample comprises heating the training samples and the unknown samples at about 100° C. to about 225° C. for about 60 to about 5 minutes, particularly about 120° C. to about 180° C. for about 10 to about 5 minutes, or any equivalent time-temperature thermal treatment regimen (profile).

The embodiments of the present invention may be used to improve resin-wood composite processing efficiency in a variety of manners. For example, they can be used to non-invasively monitor and improve a number of process variables, such as blending efficiency, blender impeller rotational speed, throughput, atomizer rpm, and resin temperature, or any combinations thereof and the like. The invention is applicable to pre-pressed and post-pressed resin-wood composites composition sampling and analyses.

The present invention is particularly applicable to the manufacture of resin-ligno-cellulosic composite board products. This invention is particularly applicable to the manufacture of multi-layered board materials in which the constituent layers or plies are composites of small wood pieces, such as wood strands, flakes, chips, wafers, slivers, or particles, or the like, which are bound together with a binder resin. This invention is especially applicable to the manufacture of oriented strand board (OSB), but it is not limited thereto, as multi-layered wafer boards, flake boards, particle boards, and the like, are also encompassed by the invention. The multi-layered boards manufactured by this invention can be used advantageously as a general construction material for exposed or covered flooring, concrete forms, sheathing, walls, roofing, cabinet work, furniture, and so forth.

DETAILED DESCRIPTION OF THE PREFERRED EMBODIMENTS

Figure 1:
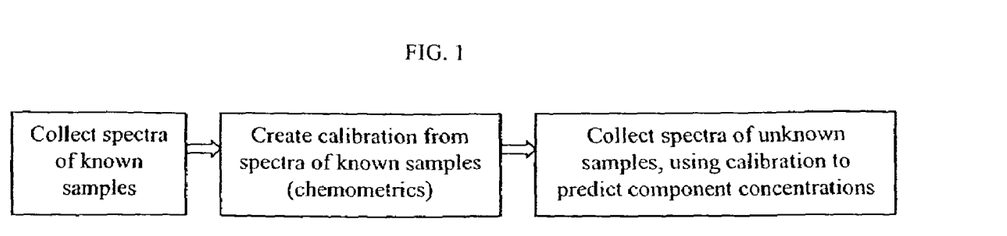
FIG. 1 is a general flow chart of a method for calibrating and quantitatively analyzing compositions of resin-wood composites using NIR spectroscopy according to an embodiment of the invention.

Referring to FIG. 1, a general method is shown for calibrating and quantitatively analyzing compositions of resin-wood composites using NIR spectroscopy according to an embodiment of the invention. For purposes herein, "calibration" refers to model development in which a series of representative samples are analyzed spectrally and the resultant data evaluated statistically. Once a valid set of spectral data exists, it serves as a predictive data set for future determinations for compositions of unknown samples. The predictive sample set includes examples of historically observed variation in the manufacturing process. For predictable quantitation, the initial sample set includes compositions comprised of ingredients in respective known concentrations. The statistics applied to the chemical and spectral properties for analytical purposes are referred to herein as "chemometrics." Calibration equations are generated which relate component absorbance with predicted concentration of each of multiple components constituting unknown resin-wood composite compositions.

Referring still to FIG. 1, in this embodiment, sample analysis by NIR spectroscopy is performed under three principal steps. After calibration of the instrument with spectra of samples whose composition is known, the spectra of unknown samples can be compared to the calibration samples to determine the component concentrations. The calibration and comparisons are performed by chemometric analysis, a statistical method for analyzing spectral data, of the spectral data. Software packages for chemometric analysis are commercially available which may be adapted to perform this step. This type of calibration differs from traditional quantitative spectral methods in that the absorbance across the entire NIR spectrum range can be used in the analysis, rather than at a single or only several wavelengths.

Unlike prior procedures involving the use of NIR spectroscopy to measure resin content in engineered wood products which also remove absorptive effects of water prior to analyzing the NIR spectra, the inventive methods make it possible to measure simultaneously the resin content of one or multiple resins present, wax content, moisture content of ground flakes, and concentrations of other ingredients, without unusual modifications to the spectral data. This result is not expected, in that many of the measurable components of interest are present in relatively small amounts in a wood matrix, which is also spectroscopically active. One might expect that nearly all of the spectral intensity would be due to wood functionalities, which may overlap or obscure signals of interest for the other components. To illustrate this point, phenolic resin, used as a binder for wood composites, and lignin, a component of wood, both have phenol rings as part of their structure. The use of chemometric techniques makes it possible to develop spectral calibrations for components present in amounts as small as 1%, or lower to 0.5%. Quantitative measurement of moisture content (free and bound) is critical as the bonding quality achieved in the pressed composite product is a direct function of moisture content in the resin-wood premixtures presented to the pressing operation.

It would be more convenient to have an instrument that collects a full spectrum in the NIR range, making filters a non-issue, especially if process formulation changes are expected. Full spectrum analysis can also provide a more robust calibration due to the variability of wood itself. Different species may have different spectral features, which could interfere with additive detection if they occurred at wavelengths being measured. With full spectrum analysis, species variation (or other kinds of expected variation) can be built into the calibration and thus not interfere with attainment of accurate measurements.

Figure 2:
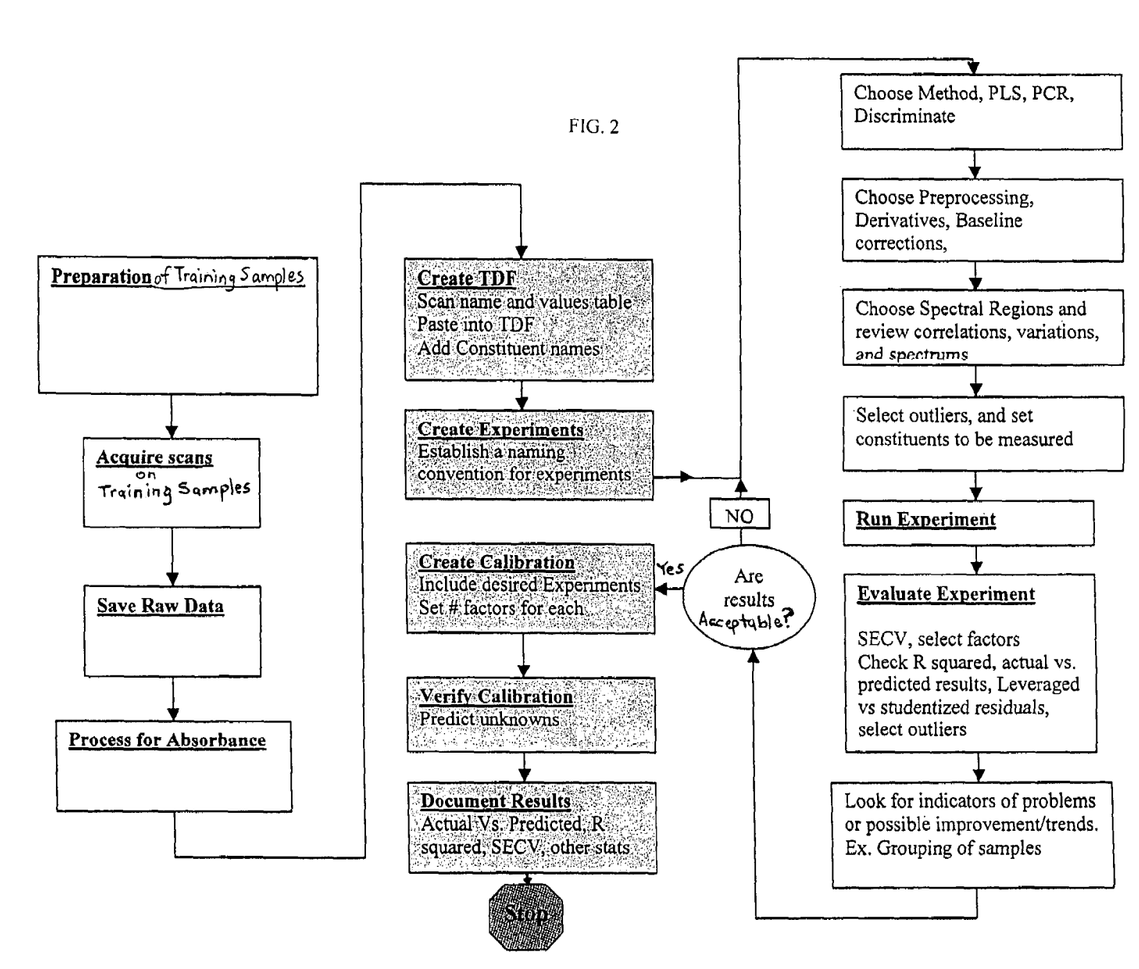
FIG. 2 is a more detailed flow chart of a method for calibrating and quantitatively analyzing compositions of resin-wood composites using NIR spectroscopy according to an embodiment of the invention.

FIG. 2 shows a more detailed flow chart for implementing the inventive method, and its features will be better understood from the detailed discussions below. For example, in one exemplary implementation of the inventive method, the basic steps include: 1) determine goals and identify key model parameters; 2) create a training set of wood-resin compositions of known component concentrations; 3) create a training data file; 4) set up experiments for testing calibration models; 5) run experiments using the diagnostic models; 6) examine model diagnostics and statistics; 7) modify and re-run experiments; 8) build a calibration; 9) predict unknown samples of wood-resin compositions; and 10), optionally, automate prediction on unknown samples.

Information about each and every component of a sample is contained in its NIR spectrum. When building a calibration, the software measures changes in these spectra relative to the others in the training set. The software algorithms then generate a calibration model by iterative processes in which the values of error functions are reduced. The result is a model or models in which spectral changes correlate with the changes in each component or property which is desired to be measured, based on the component or property levels provided as input. As long as multiple components or properties do not vary in a collinear fashion, the calibration models are specific for particular components or properties. Theoretically, a calibration can be built for any measured component or property of the sample, given a properly constructed training data set. However, it is up to the user to evaluate the quality of the given model, based on factors such as error functions, statistical tests, and outliers, and decide whether it is acceptable for use.

In practicing the present invention, an OSB or other ligno-cellulosic formulation blend samples, as uncured mixtures, are prepared having known concentrations of resin, wax, additives, moisture, and optionally other additives such as inorganic cure accelerators, polyols, fire retardants, etc., in which the range of each component concentration spans a predetermined expected possible range for that component. Each sample contains all components to be measured. At least 10, and preferably more than 15 samples are prepared with various range amounts of the respective components. The concentration of each component in each sample is chosen randomly. In one particular embodiment, at least 20 samples are prepared. A non-limiting example set of 20 samples, in which the amount of resin varies from 0-10%, and wax varies from 0-5%, is shown below.

TABLE 1

| sample no. | % resin | % wax |
|---|---|---|
| 1 | 8.99 | 2.46 |
| 2 | 3.10 | 1.03 |
| 3 | 9.75 | 4.89 |
| 4 | 0.12 | 1.90 |
| 5 | 7.35 | 4.18 |
| 6 | 3.73 | 3.15 |
| 7 | 1.09 | 3.58 |
| 8 | 9.40 | 2.51 |
| 9 | 1.80 | 2.97 |
| 10 | 1.40 | 2.93 |
| 11 | 6.95 | 1.41 |
| 12 | 0.31 | 4.35 |
| 13 | 4.47 | 3.99 |
| 14 | 5.58 | 3.90 |
| 15 | 8.23 | 1.19 |
| 16 | 1.48 | 0.27 |
| 17 | 7.24 | 3.52 |
| 18 | 3.36 | 4.16 |
| 19 | 8.51 | 1.29 |
| 20 | 0.49 | 1.15 |

The wood used in these samples may be OSB flakes ground into pieces smaller than 0.25 inch. The components (resin adhesive(s), slack wax, emulsion wax, polyol, inorganic cure accelerator, etc.) are then precisely weighed into a known amount of ground wood flakes. Then the sample is mixed in a kitchen-style blender or other suitable blending apparatus until a homogeneous mixture results. After mixing, the portion of the sample passing a 0.85 mm screen is collected.

Near-infrared spectra is collected on the <0.85 mm portion of each sample. After scanning, the moisture content of each sample is measured by weight loss after heating to dryness, so that the component concentrations relative to the oven-dry wood weight can be calculated. In the illustrations provided herein, the test samples are ground prior to NIR scanning. However, it will be appreciated that different sampling techniques may also be used which make grinding unnecessary as part of the sample preparation for NIR scanning.

The near-infrared instrument used in these experiments may be an LT Industries, Inc. (Gaithersburg, Md.) IsoChem Near-infrared Analyzer, with a user interface controlled by ThermoGalactic's (Waltham, Mass.) GRAMS/AI software package for instrument control, PLS Plus/IQ for calibration model building, and IQ Predict for predicting concentrations of unknown samples. Other near-infrared analyzers and user interface software also could be used to obtain similar results. Each spectrum collected is an average of multiple, e.g., about 20-25, particularly about 25, single-scan spectra, but a different number of scans may be averaged to obtain identical results. Training data files can be created in Microsoft Excel™ spreadsheets for use inputting the training set formulations when using programs such as ThermoGalactic's GRAMS/AI software package.

The near-IR spectra of the known samples are treated by a chemometric analysis software package to create a calibration for each component of interest. The main steps of this procedure involved providing the concentrations of each component (based on oven-dry wood weight) of interest for the spectrum of each sample and selecting options for data treatment. The chemometric software package used for this example may be the ThermoGalactic's PLS plus/IQ software, but other software packages could be used to obtain similar results. As generally known, PLS uses the constituent values during the principal component decomposition to "weight" the calibration spectra. The result is a series of calibration equations; one for each PLS principal component, where the principal components are directly related to the constituents of interest. The ThermoGalactic's PLS plus/IQ software packages permits the operator to select the calibration type and number of model factors. The software calibration types may be selected from, e.g., PLS-1, PLS-2, PCR, PCA, and discriminate. PLS-1 is preferred. It is important to use enough factors to adequately model the data and avoid underfitting, but not too many that could lead to poorer predictions of unknowns.

The diagnostic type also may be selected from the software. It is employed to validate the calibration equations, but cross-validation is preferred. Cross validation attempts to emulate predicting "unknown" samples by using the training set data itself. One or more samples are left out during the calculation, then predicted back with the model. This process is repeated until all samples have been left out. This validation approach provides better accuracy in prediction of true unknowns and better outlier prediction. Limited data preparation may be applied such as the "Mean Center" option in PLSplus/IQ software. However, data pre-processing algorithms generally need not be applied to remove interferences in data in terms of path length corrections, baseline corrections and statistical corrections, for the wood-resin chemistries of interest. Desired spectral region selections and settings and exclusion of outliers can be performed in PLSplus/IQ software via graphical user-interface. Removal of outliers, i.e. samples within the training set which do not fit, usually improves the predictive ability of the developed model and avoids introduction of bias in the model. Outliers often arise from errors when creating the training set (e.g., transcription error, spectrometer error, etc). Many commercial chemometric modeling software programs such as PLSplus/IQ software include statistical tools, e.g., Mahalanobis distance, F-ratio and F-statistic, to assist a user in identifying outliers. The training set also should be examined for collinearity. Plots of two different constituents are collinear if the concentration for one constituent is a linear function of the concentration of another. If a training set is collinear, unknowns may not be predicted properly.

To quantitatively analyze unknown wood-resin samples using the validated calibration equations, samples of unknown component concentrations may then be ground and NIR spectra are collected, preferably on the <0.85-mm fraction. A routine within the chemometric software compares spectra of unknown samples to the calibration set and predicts the concentrations of the components of the samples. Statistical measures of the similarity of the unknown spectrum to the calibration set indicate how well each spectrum matches the data in the calibration set, and by extension how reliable was the prediction.

In another embodiment of the present invention, it has been discovered that measurement predictability for aged samples is significantly improved by thermally pre-treating training samples and unknown samples at temperatures above room temperature immediately prior to spectroscopic analysis. In one embodiment, the irradiating of the unknown sample occurs at least about four hours, particularly at least about 24 hours, and more particularly about 24 to about 240 hours, after admixture of the components thereof.

In one embodiment, the heating of the training samples and the heating of the unknown sample comprises heating the training samples and the unknown samples at about 100° C. to about 225° C. for about 60 to about 5 minutes, particularly about 120° C. to about 180° C. for about 10 to about 5 minutes, or any equivalent time-temperature thermal treatment regimen (profile).

The embodiments of the present invention may be used to improve resin-wood composite processing efficiency in a variety of manners. For example, they can be used to non-invasively monitor and improve a number of process variables, such as blending efficiency, blender rotational speed, throughput, atomizer rpm, and resin temperature, or any combinations thereof and the like. The invention is applicable to pre-pressed and post-pressed resin-wood composites composition sampling and analyses.

The resin-wood composite products that can be noninvasively quantitatively analyzed for composition by NIR spectroscopic methods of the present invention are not particularly limited.

For instance, resin-wood ligno-cellulosic composites include composite materials such as oriented strand board, wafer board, chipboard, fiberboard, etc. Ligno-cellulosic materials may be derived from naturally occurring hard or soft woods, singularly or mixed, whether such wood is green or dried. Typically, the raw wood starting materials, either virgin or reclaimed, are cut into strands, wafers or particles of desired size and shape. These ligno-cellulosic wood materials can be "green" (e.g., having a moisture content of 5-30% by weight) or dried, wherein the dried materials have a moisture content of about 2-18 wt %. Preferably, the ligno-cellulosic wood materials comprise dry wood parts having a moisture content of about 3 to 14 wt %. The dry wood parts are typically 0.01 to 0.5 inches thick, although thinner and thicker wood materials can be used in some applications. Moreover, these wood materials are typically less than one inch to several inches long and less than one inch to a few inches wide.

In commercial manufacture of oriented strand board (OSB) panels, e.g., ligno-cellulosic wood materials are coated with a curable polymeric thermosetting binder resin and wax additive, such that the wax and resin effectively coat the wood materials. The resin component that may be used in these mixtures include, but are not limited to, phenol-formaldehyde resin (powdered or liquid), isocyanates, such as 4,4'-diphenylmethane diisocyanate (MDI) and polymeric versions of MDI (pMDI), melamine-formaldehyde resin, melamine-urea-formaldehyde resin, melamine-urea-phenol-formaldehyde resin, soy-protein based resins, and combinations thereof. Preferred binders include polymeric 4,4'-diphenyl-methane diisocyanate (pMDI) and phenol formaldehyde (powder or liquid). The binder loading level is preferably in the range of 1-10 wt %, based upon the oven-dried wood weight, more preferably 2-5 wt %.

Other additives can also be used to add functionality, improve properties, or increase manufacturing rates. These additives are materials such as waxes, polyols, inorganic or organic curing accelerators, fire retardants, recycled sanding dust, fillers, etc. A wax additive is commonly employed to enhance the resistance of the OSB panels to absorb moisture. Preferred waxes are slack wax or a micro-crystalline wax. The wax loading level is preferably in the range of 0.5-2.5 wt %, based upon the oven-dried wood weight.

Alumina trihydrate (ATH), also known as aluminum hydroxide, is commonly used as both a filler and a fire retardant in these synthetic polymeric materials and can be identified by the chemical formulae of $Al(OH)_3$ or $Al_2O_3 \cdot 3H_2O$. As a result of its well-known fire retardant properties, the use of alumina trihydrate as a particle filler results in a highly flame resistant polymeric product.

Conventionally, the binder, wax, polyols, inorganic curing accelerators, fire retardants, etc., and any other additives are applied to the wood materials by various spraying techniques. One such technique is to spray the wax, resin and additives upon the wood strands as the strands are tumbled in a drum blender. These ingredients may be added via spray or otherwise into the drum blender so that at least a portion of the additives will coat the wood materials. The spray technique may be, for example, by use of electric atomizers, hydraulic or pneumatic sprayers, etc. Binder resin and various additives applied to the wood materials are referred to herein as a coating, even though the binder and additives may be in the form of small particles, such as atomized particles or solid particles, which may not form a continuous coating upon the wood material.

The blended mixture is formed into either a random mat or oriented multi-layered mats. In particular, the coated wood materials are spread on a conveyor belt in a series of alternating layers, where one layer will have the flakes oriented generally in line with the conveyor belt, and the succeeding layer oriented generally perpendicular to the belt, such that alternating layers have coated wood materials oriented in generally a perpendicular fashion. Subsequently, the formed mats are pressed under a hot press machine, which fuses and binds together the coated wood materials to form a consolidated OSB panels of various thickness and size. Preferably, the panels of the invention are pressed for 2-10 minutes at a temperature of about 325 to about 500 degrees Fahrenheit. The resulting composite panels may have a density in the range of about 38-50 pcf (ASTM D1037-98) and a thickness of about 0.25 inch to about 1.5 inch, depending on the composition and press conditions.

The examples that follow are intended to further illustrate, and not limit, embodiments in accordance with the invention. All percentages, ratios, parts, and amounts used and described herein are by weight unless indicated otherwise.

EXAMPLES

Example 1

The use of NIR spectroscopy to quantitatively measure the amount of resin, wax, and moisture in OSB was investigated. The protocols used were as follows.

A model for determining the concentration of MDI, wax, powdered phenolic resin, and moisture in ground flake samples was constructed by preparing samples of known concentrations of these components in the laboratory. Dry flakes (3-12% moisture content; at least 85% southern pine content) were obtained from an OSB mill in Commerce, Ga. and ground to pass 0.25 inch screen. MDI, wax, and powdered phenolic resin were added in specific amounts to ground flake samples of precisely known weight. Each sample had different contents of each of the components, and component concentrations were randomly chosen from within a range for each sample (Table 2 gives the ranges for each component). The mixtures were each blended until good mixing was achieved. The near-infrared spectrum between 1200 and 2400 nm was collected on the portion of the sample passing a 0.85-mm sieve. After scanning, the moisture content of each sample was measured by weight loss after heating to dryness. A calibration was built using chemometric methods (GRAMS software with PLS plus-IQ subroutine) and 163 spectra, representing 154 unique samples. The calibration was validated using a set of 41 spectra (39 unique samples). Table 3 presents a summary of the calibration and validation set statistics.

TABLE 2

Component concentration range for calibration samples.

| Component | Range (% of OD wood) |
|---|---|
| MDI | 0-12.80 |
| Wax | 0-5.63 |
| Powdered phenol-formaldehyde resin | 0-6.76 |
| Moisture content | 2.97-11.57 |

TABLE 3

Statistical information for calibration and validation samples.

| | | | Calibration | Validation |
|---|---|---|---|---|
| Component | Factors | SECV | $R^2$ (adj) of actual vs. predicted values | $R^2$ (adj) of actual vs. predicted values |
| MDI | 8 | 0.722 | 0.954 | 0.956 |
| Wax | 8 | 0.520 | 0.833 | 0.890 |
| Powdered phenol-formaldehyde resin | 8 | 0.408 | 0.950 | 0.963 |
| Moisture content | 6 | 0.298 | 0.970 | 0.954 |

Example 2

MDI concentrations in flake samples from the Commerce, Ga. (3-12% moisture content; at least 85% southern pine content) mill were calculated in two ways.

The samples were ground and scanned by a LT Instruments NIR spectrometer according to established procedure. The resulting spectra were analyzed by chemometric software, based on an existing library of similar flake samples, to predict the MDI concentrations of the unknown samples.

The same samples that were scanned by NIR in method 1 were sent to a third-party laboratory (Atlantic Microlab, Norcross, Ga.) for analysis of nitrogen content. A flake sample without adhesive was also submitted to establish a background level of nitrogen in the samples. The background amount was subtracted from all the other samples before calculations were performed. A sample of neat MDI was also analyzed for its nitrogen content. The MDI content of the flakes was calculated based on the nitrogen content of the flakes.

Figure 3:
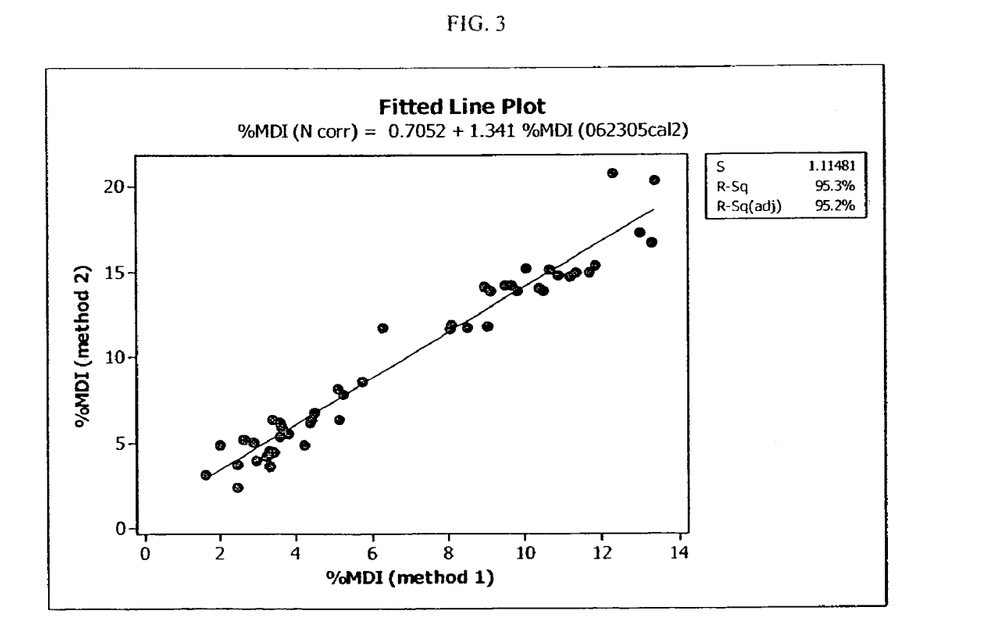
FIG. 3 is a fitted line plot comparing resin (MDI) concentration prediction by NIR model prediction ("method 1") in an example described herein according to an embodiment of the present invention versus nitrogen levels measured by elemental analysis ("method 2").

The MDI values calculated by methods 1 and 2 are plotted in FIG. 3, in which the X axis is MDI concentration from NIR model prediction, and the Y axis is the MDI concentration based on nitrogen levels measured by elemental analysis.

If the agreement between the two measurement systems were perfect, the regression plot would have an $R^2$ of 1.000. In this example, the linear fit was a good one, as evidenced by the 95% $R^2$ value.

Example 3

The effects of heating wood composite samples for different time-temperature profiles prior to NIR analysis were investigated.

In one set of experiments, ten samples of wood flakes from an OSB mill in Easton, Me. (3-12% moisture content; at least 75% aspen content) were mixed with varying amounts of MDI, slack wax, and powdered phenolic resin. These samples were screened to remove particles larger than 0.85 mm; the portion smaller than 0.85 mm was divided into 2 g portions. The portions were heated for 1, 5, 10, or 30 minutes at 200° C. within a time period not exceeding 4 hours after the wood flakes were mixed with the other components. An unheated portion of each sample was also set aside as a control.

Spectral calibrations were built for each heating time using these spectra. The steps involved were: 1) Preparing a calibration set of samples containing flakes (wood), resin, wax, and and/or other relevant components in amounts comparable to those observed in production samples; 2) Heating the calibration samples for a specified period of time at a specified temperature; 3) Allowing the calibration samples to cool to room temperature and collect their NIR spectra; 4) Using chemometric techniques, build a calibration based on the NIR spectra of the calibration samples; 5) Obtaining unknown samples and heat at the same conditions as the calibration samples; 6) Collecting NIR spectra of unknown samples; and 7) using the calibration to predict the component levels.

Figure 4:
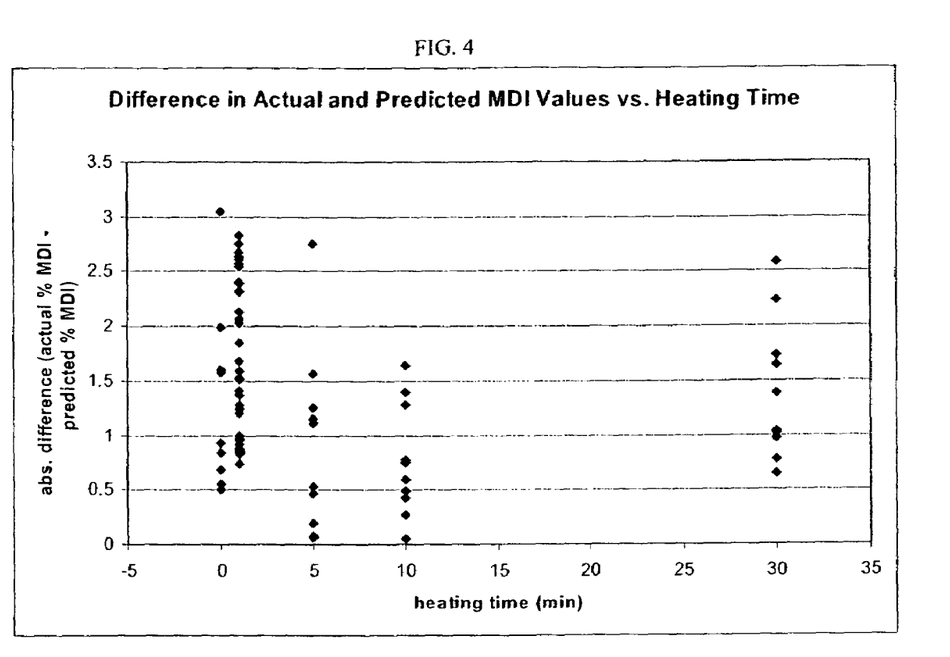
FIG. 4 is a plot showing differences in actual and predicted MDI values versus preheating times applied before conducting spectral analysis based results of an example described herein.

As to the results obtained, each calibration displayed a standard error of cross validation (SECV) of less than 0.5 and an $R^2$ for actual versus predicted values of greater than 0.98, indicating that the data and calibrations are of good quality. The samples were held in plastic zipper bags for 8 days, and then rescanned. The calibrations based on spectra of the samples collected just after heating and cooling were used to predict the concentrations of MDI, wax, and powdered phenolic resins from the spectra of same samples collected eight days later. FIG. 4 shows the differences in the actual concentration and the calibration-predicted concentrations.

When the samples were not heated (0 min heating time, above), held for eight days, and then rescanned, the predicted values based on the new scans were different from the actual values by as much as 3% (MDI values were calculated with respect to dry wood weight in both cases). After heating the samples for 1 minute, the differences between actual and predicted values were similar, but when heated for 5 (but for one outlier) or 10 minutes, the maximum difference between actual and predicted values was about 1.6%. When heated for 30 minutes, the maximum difference between actual and predicted values increases to around 2.5%. This illustrates that heating the samples can stabilize them for some period of time, thus allowing sample preparation and analysis to be separated in time. However, heating too long decreases the precision of the predicted measurements at the temperature used here. Optimal heating times may vary with temperature.

While the invention has been particularly described with specific reference to particular process and product embodiments, it will be appreciated that various alterations, modifications and adaptations may be based on the present disclosure, and are intended to be within the spirit and scope of the present invention as defined by the following claims.

What is claimed is:

1. A method for determining the composition of a resin-wood composite material, comprising:
   providing a plurality of training samples comprising a mixture of quantitatively predetermined respective amounts of a plurality of components comprising at least wood, resin, moisture, and wax;
   irradiating said plurality of training samples with NIR radiation using NIR spectroscopic instrumentation including an associated source of NIR radiation, wherein said irradiating comprises exposing said training samples to NIR radiation at a succession of different wavelength values spanning a selected spectral range of wavelengths including a range of about 1200 nm to about 2400 nm;
   measuring non-absorbed NIR energy reflected by said exposed training samples over said selected spectral range at wavelength measuring intervals not exceeding about 5 nm, providing respective training sample spectral data sets;
   generating a calibration with reference to the training sample spectral data sets for the NIR spectroscopic instrumentation for quantitatively correlating spectral results with component concentrations in compositions comprising a mixture of at least wood, resin, moisture, and wax;
   irradiating at least one test sample comprising a mixture of quantitatively unknown amounts of a plurality of components comprising at least wood, resin, moisture, and wax, with NIR radiation using the NIR spectroscopic instrumentation, wherein said irradiating comprises exposing said test sample to unfiltered NIR radiation at a succession of different wavelength values spanning a selected spectral range of wavelengths including a range of about 1200 nm to about 2400 nm;
   measuring non-absorbed NIR energy reflected by said test sample over said selected spectral range at wavelength measuring intervals not exceeding about 5 nm, providing a test sample spectral data set; and
   predicting, using the calibration and the test sample spectral data, component concentrations of at least resin, moisture, and wax, in the test sample.

2. The method of claim 1, wherein the respective amounts of the components of the training samples are randomly chosen for each training sample within a respective preselected range for each of said components.

3. The method of claim 1, wherein the training samples and test sample are provided at approximately the same temperature for the respective steps of irradiating them with NIR radiation.

4. The method of claim 1, wherein a plurality of scans are taken at each measurement interval for the training samples, and the results are averaged to provide a respective average non-absorbed energy value at each given measurement wavelength which are referenced in generating the calibration.

5. The method of claim 1, wherein a plurality of scans are taken at each measurement interval for the test sample, and the results are averaged to provide a respective average non-absorbed energy value at each given measurement wavelength that is referenced in the predicting of the component concentrations of the test sample.

6. The method of claim 1, wherein about 20 to about 40 scans are taken at each measurement interval for the training samples, and the results are averaged to provide a respective average non-absorbed energy value at each given measurement wavelength which are referenced in generating the calibration.

7. The method of claim 1, wherein about 20 to about 40 scans are taken at each measurement interval for the test sample, and the results are averaged to provide a respective average non-absorbed energy value at each given measurement wavelength that is referenced in the predicting of the component concentrations of the test sample.

8. The method of claim 1, wherein the NIR spectroscopic instrumentation comprises a rapid-scanning grating system operable to use a diffraction grating to separate a polychromatic spectrum into constituent wavelengths.

9. The method of claim 1, wherein said generating of the calibration comprises applying multivariate data analysis to the training sample spectral data sets.

10. The method of claim 9, wherein the multivariate data analysis is selected from the group consisting of partial least squares regression (PLS), principal component analysis (PCA), principal component regression (PCR), multilinear regression analysis (MLR).

11. The method of claim 9, wherein the multivariate data analysis comprises partial least squares regression (PLS).

12. The method of claim 1, wherein the resin includes phenol formaldehyde resin and isocyanate resin.

13. The method of claim 1, wherein the wood component comprises a wood material selected from the group consisting of wood strands, wood flakes, wood particles, sawdust, wood wafers, and wood fibers.

14. A method for determining the composition of a resin-wood composite material, comprising:
providing a plurality of training samples comprising quantitatively predetermined respective amounts of a plurality of components comprising at least wood, resin, moisture, and wax;
heating the training samples for a temperature and time sufficient to stabilize the training samples for spectral analysis;
irradiating said plurality of heated training samples with NIR radiation using NIR spectroscopic instrumentation including an associated source of NIR radiation, wherein said irradiating comprises exposing said heated training samples to unfiltered NIR radiation at a succession of different wavelength values spanning a selected spectral range of wavelengths including a range of about 1200 nm to about 2400 nm;
measuring non-absorbed NIR energy reflected by said exposed heated training samples over said selected spectral range at wavelength measuring intervals not exceeding about 5 nm, providing respective training sample spectral data sets;
generating a calibration with reference to the training sample spectral data sets for the NIR spectroscopic instrumentation for quantitatively correlating spectral results with component concentrations in compositions comprising at least wood, resin, moisture, and wax;
heating a test sample comprising quantitatively unknown amounts of a plurality of components comprising at least wood, resin, moisture, and wax, for a temperature and time sufficient to stabilize the test sample for spectral analysis;
irradiating at least one test sample comprising quantitatively unknown amounts of a plurality of components comprising at least wood, resin, moisture, and wax with NIR radiation using the NIR spectroscopic instrumentation, wherein said irradiating comprises exposing said test sample to unfiltered NIR radiation at a succession of different wavelength values spanning a selected spectral range of wavelengths including a range of about 1200 nm to about 2400 nm;
measuring non-absorbed NIR energy reflected by said test sample over said selected spectral range at wavelength measuring intervals not exceeding about 5 nm, providing a test sample spectral data set; and
predicting, using the calibration and test sample spectral data set, component concentrations of at least resin, moisture, and wax, in the test sample.

15. The method of claim 14, wherein the irradiating of the test sample occurs at least about four hours after admixture of the components thereof.

16. The method of claim 14, wherein the irradiating of the test sample occurs at least about 24 hours after admixture of the components thereof.

17. The method of claim 14, wherein the irradiating of the test sample occurs about 24 hours to about 240 hours after admixture of the components thereof.

18. The method of claim 14, wherein the heating of the training samples and the heating of the test sample comprises heating the training samples and the unknown samples at about 100° C. to about 225° C. for about 60 to about 5 minutes.

19. The method of claim 14, wherein the heating of the training samples and the heating of the test sample comprises heating the training samples and the unknown samples at about 120° C. to about 180° C. for about 10 to about 5 minutes.

20. The method of claim 14, wherein the training samples and test sample are provided at approximately the same temperature for the respective steps of irradiating them with NIR radiation.

21. The method of claim 14, wherein said generating of the calibration comprises applying multivariate data analysis to the training sample spectral data sets.

22. A method for making an engineered wood product, comprising:
(a) providing a plurality of training samples comprising a mixture of quantitatively predetermined respective amounts of a plurality of components comprising at least wood, resin, moisture, and wax;
(b) irradiating said plurality of training samples with NIR radiation using NIR spectroscopic instrumentation including an associated source of NIR radiation, wherein said irradiating comprises exposing said training samples to NIR radiation at a succession of different wavelength values spanning a selected spectral range of wavelengths including a range of about 1200 nm to about 2400 nm;
(c) measuring non-absorbed NIR energy reflected by said exposed training samples over said selected spectral range at wavelength measuring intervals not exceeding about 5 nm, providing respective training sample spectral data sets;
(d) generating a calibration with reference to the training sample spectral data sets for the NIR spectroscopic instrumentation for quantitatively correlating spectral results with component concentrations in compositions comprising a mixture of at least wood, resin, moisture, and wax;
(e) preparing a resin-wood composite composition comprising a mixture of a plurality of components comprising at least wood, resin, moisture, and wax;
(f) withdrawing a portion of the resin-wood composite composition to provide a test sample;
(g) irradiating the test sample with NIR radiation using the NIR spectroscopic instrumentation, wherein said irradiating comprises exposing said test sample to unfiltered NIR radiation at a succession of different wavelength values spanning a selected spectral range of wavelengths including a range of about 1200 nm to about 2400 nm;

(h) measuring non-absorbed NIR energy reflected by said test sample over said selected spectral range at wavelength measuring intervals not exceeding about 5 nm, providing a test sample spectral data set; and
(i) predicting, using the calibration and the test sample spectral data, component concentrations of at least resin, moisture, and wax, in the test sample;
(j) comparing the predicted component concentrations to target component concentrations therefor;
(k) adjusting, if necessary, component concentrations of the resin-wood composite composition to coincide with the corresponding target concentrations;
(l) optionally repeating steps (f)-(k) at least once;
(m) forming a unitary composite member from the resin-wood composite composition.

* * * * *